United States Patent [19]

Dildine

[11] Patent Number: 4,571,271

[45] Date of Patent: Feb. 18, 1986

[54] METHOD OF REMOVING SEDIMENT FROM A LARGE STORAGE CONTAINER

[76] Inventor: Gerald R. Dildine, 1112 Maple St., Collinsville, Okla. 74021

[21] Appl. No.: 644,456

[22] Filed: Aug. 27, 1984

[51] Int. Cl.⁴ .......................... B08B 5/04; B08B 9/08
[52] U.S. Cl. ........................................ 134/21; 15/1.7; 134/22.1; 210/803; 405/74; 405/185
[58] Field of Search .................... 134/21, 22.1, 22.18; 15/1.7; 210/803; 405/74, 185

[56] References Cited

U.S. PATENT DOCUMENTS

| | | | |
|---|---|---|---|
| 867,984 | 10/1907 | Lake | 405/185 X |
| 3,003,169 | 10/1961 | Forrester | 15/1.7 |
| 3,961,393 | 6/1976 | Pansini | 15/1.7 |
| 4,240,173 | 12/1980 | Sherrill | 15/1.7 |
| 4,314,521 | 2/1982 | Lundberg | 15/1.7 X |

*Primary Examiner*—Marc L. Caroff
*Attorney, Agent, or Firm*—Walter M. Benjamin

[57] ABSTRACT

Disclosed is a method of cleaning sediment from the bottom of a large storage container of clean water comprising sanitizing a cleaning person and a suction pump to remove the majority of skin viruses, germs, bacteria and dirt from the surface of his skin and/or apparel and the suction pump; the cleaning person going underwater and slowly submerging; the cleaning person turning on the suction pump before reaching the bottom of the container; the cleaning person removing sediment from a spot on the bottom of the container before any part of his body disturbs the sediment; the cleaning person attaining footing in the clean spot; and the cleaning person removing the remainder of the sediment on the bottom of the container.

14 Claims, No Drawings

METHOD OF REMOVING SEDIMENT FROM A LARGE STORAGE CONTAINER

BACKGROUND OF THE INVENTION

1. Field of the Invention

This invention relates to a method of cleaning a large storage container of clean water, more particularly this invention relates to a method of cleaning a large storage tank of clean water and even more particularly this invention relates to a method of cleaning a large storage tank of drinking water.

2. Brief Description of the Prior Art

Clean water has been stored by various large storage techniques such as ponds, lakes, reservoirs, cisterns, tanks, etc. for various reasons as an integral part of a water system. These reasons include water usage, source variance, energy availability, gravity flow, gravity pressurization, fire fighting, blackouts, and other emergency situations. Of all the storage techniques, tanks are the best in terms of convenience, protection against contamination, shielding from sunlight, and ease in determining the amount of water stored.

For high water quality control and for insurance of the integrity of its container, it is necessary to perform periodic cleaning of the container. In the bottom of all of these storage means gunk and muck will accumulate coating its bottom. An open container or a poorly covered one will always allow dirt, leaves, insects, lizards, and mice into the water system. The incoming water into the storage container may carry its own sediment, held in suspension, which, in the tranquil waters of the tank, will precipitate. Some minerals as well will, upon contact with air, precipitate out in the storage container. Many times deteriation of the container or its coating or liner can cause sediment in the bottom of the container and/or contaminate the water or cause it to be distaseful or discolored.

Because of the importance in avoiding dirtying or contaminating the water, the most convenient and primary storage containers have been difficult to clean while they contain a large amount of water. By primary container it is meant one that contains water that requires no treatment before use. The large size of the container and the fear of disturbing sediment and deposists on the bottom and walls of the container have made cleaning the interior of a filled container impractical. Consequently, heretofore, these containers had to be emptied before a thorough cleaning could be done. However it is undesirable to completely empty such a container because of the need of a temporary means of holding the water. If the water is disposed of during the cleaning, water is not available for emergency use.

SUMMARY OF THE INVENTION

It has been found that a large primary storage container of water can be thoroughly cleaned of sediment without dirtying or contaminating the water and without emptying the container. Accordingly the container is cleaned by (1) sanitizing the entire body and/or appearel of the cleaning person and his equipment of surface viruses, germs, bacteria and dirt; (2) the cleaning person physically going underwater into the interior of the container with a suction pump; (3) the cleaning person turning on the suction pump before he reaches the bottom of the container; (4) the cleaning person cleaning a spot on the bottom of the container with the suction pump without any part of his body disturb the sediment on the bottom; (4) the cleaning person gaining footing on the clean spot; and (5) the cleaning person cleaning the remainder of the bottom of the container with the suction pump. All of his cleaning equipment that he takes with him underwater is sanitized as well. It has been found that an entire diving apparatus, including an above water supplied or self contained breathing apparatus, can be sanitized and used by the cleaning person to allow him to stay underwater throughout the entire cleaning process without coming up for air.

DESCRIPTION OF THE PREFERRED EMBODIMENTS

According to the present invention large storage containers of clean water can be cleaned without emptying the container and without contaminating or dirtying the water. The particular type of storage container of clean water that is cleaned by the present invention are containers that cannot be cleaned from above the surface of the water therein and which cannot be cleaned from any part of its exterior. Such containers are used for primary water storage, that is, water that needs no treatment or that has been treated and ready for use for normal human consumption and home use. Most ofter these containers are clean water storage tanks made from wood, metal, plastic or concrete but are not limited exclusively thereto. The main concern is containers that have an interior surface that, unless periodically checked, repaired and cleaned, will cause the water to fall below quality standards.

By clean water it is meant water that is fit for human consumption and use including such things as drinking, cooking, washing dishes and clothes, bathing, flushing toilets, irrigation, etc. While some of these uses do not require as clean water as others, containers of water that we know of as tap water has been used for all these purposes and can be cleaned by the present invention. While this invention can be used for cleaning containers storing water for all of these purposes and some industrial purposes, it will become apparent that it is most useful for water that, without further purifying treatment, will be used for human consumption.

Further in accordance with the present invention the cleaning person will completely sanitize his entire body and/or appearal of the majority of surface viruses, germs and bacteria as well as normal body dirt. This is accomplished by soaking for between 0 and 15 minutes and then washing and scrubbing with between 0.2 and 0.5 percent by weight sodium hypochlorite in solution. Sanitizing can also be accomplished by spraying with a 0.2 to 0.5 percent by weight sodium hypochlorite in solution. Preferabley the highest bleach concentration without causing damage to the skin is preferred. It is understood that other expedients well known in the art can be used for removing surface viruses, germs, bacteria and dirt.

All equipment used by the cleaning person will also be sanitized by removing the majority of viruses, germs, bacteria and surface dirt therefrom. These can also be soaked for between 0 and 15 minutes and washed and scrubbed with between 0.2 and 0.5 percent sodium hypochlorite by weight in solution. This equipment can also be sprayed with a 0.2 to 0.5 percent sodium hypochlorite by weight in solution. Other expedients such as ultraviolet radiation can be used to sanitize equipment. Above water supplied and self contained underwater breathing apparatus can be useful and many times necessary to allow the cleaning person to remain underwater for long periods of time. These are also sanitized along with the other equipment.

The sanitized cleaning person physically goes underwater into the interior of the storage container of clean water, taking along a suction pump. There are many types of suction pumps but the most expedient found for the present invention is the air lift and the water ejection lift pumps well known in the art. The water ejection pump creates suction by transfering energy from a small stream of high velocity water to the general body of water in the suction pipe which it entrains as it is directed up the suction pipe. The faster this body of entrained water can be made to move the better the suction, or speed of flow at the intake. The air lift pump creates suction by creating a difference in density between a mixture of water and air in the suction pipe and the water in the container. This difference in density gives rise to a difference of pressure at the mouth of the suction pipe which increase with depth. Air is blown into near the suction end of the pipe to create the density difference.

Of the two type pumps the air lift pump is preferred as a it require less power to operate and a simple air cut off valve can be placed on the air supply pipe near the suction end of the suction pipe. This location allows the cleaning person to have local control of the air pump which may be located outside of the container. The type of pipe used for suction can be flexible and light (not requiring high pressure as the water ejection lift pump) such as flexible plastic tubing or pipe so that the cleaning person can easily maneuver the suction end to clean the container. The size of the suction pipe is between 2.0 to 8.0 inches ID and preferably between 2.5 and 3.0 inches ID. The air supply pipe is preferably 0.375 to 1.0 inches ID. The suction pipe must be big enough to pick up large size debris as well as small enough that, during the cleaning operation, a substantial amount of the water in the container is not evacuated.

The cleaning person begins by taking the suction pump and going underwater in the container and slowly submerges to the bottom without greatly disturbing the water. He then turns on the suction before he reaches the bottom and, after attaining neutral bouyancy four to six feet from the bottom, cleans a spot on the bottom of the container before any part of his body disturbes the fluidized sediment. He then gains his footing on the clean spot and proceed to clean the remainder of the bottom of the tank with the suction pump. Deposits and loose paint and lining on the side of the container can be cleaned after the bottom is completed.

It is preferred that a breathing apparatus is used as these cleaning operations can take long periods of time. All of the breathing apparatus as well as all equipment that will get into the water is sanitized as described above before entering the container.

It is understood that in describing this specific embodimemt it is not intended that the invention should be limited thereby. Various modifications can be made without departing from the inventive intent of the present invention.

What is claimed is:

1. A method of cleaning the interior of a large storage container containing clean water that is subject to the accumulation of sediment that causes the water to be distasteful, discolorful, or contaminated; comprising:
   (A) sanitizing the entire body and/or apparel of a cleaning person and a suction pump to remove the majority of viruses, germs, bacteria and dirt from the surface of his skin and/or apparel and pump;
   (B) the sanitized cleaning person taking the suction pump and physically going underwater and slowly submerging into the interior of the container;
   (C) the sanitized cleaning person turning on the suction pump before he reaches the bottom of the container;
   (D) the sanitized cleaning person cleaning a spot on the bottom of the container with the suction pump before any part of his body disturbs the sediment;
   (E) the cleaning person attaining footing on the clean spot; and
   (F) the cleaning person removing the remainder of the sediment from the bottom of the container with the suction pump.

2. The method of claim 1, wherein an underwater breathing apparatus is sanitized and the cleaning person goes underwater with this apparatus and uses the apparatus to allow his breathing underwater.

3. The method of claim 1, wherein a self contained underwater breathing apparatus is sanitized and the cleaning person goes underwater with this apparatus and uses the apparatus to allow his breathing underwater.

4. The method of claim 1, wherein the container is a clean water storage tank.

5. The method of claim 1, wherein the container is a drinking water storage tank.

6. The method of claim 1, wherein the cleaning person is sanitized with a sodium hypochlorite solution.

7. The method of claim 1, wherein the cleaning person is sanitized by soaking for 0 to 15 minutes and washing and scrubbing in a 0.2 to 0.5 percent by weight of sodium hypochlorite solution.

8. A method of cleaning a large drinking water storage container having sediment on the bottom of its interior comprising:
   (A) sanitizing a cleaning person and a suction pump by removing from his entire body and/or apparel and the pump the majority of surface viruses, germs, bacteria and dirt;
   (B) sanitizing underwater breathing apparatus by removing from its surface the majority of viruses, germs, bacteria and dirt;
   (C) equipping the cleaning person with the underwater breathing apparatus and the pump;
   (D) the said equipped person physically going underwater and slowly submerging himself into the container;
   (E) the said equipped person turning on the suction pump before reaching the bottom of the container;
   (F) the said equipped person cleaning a spot on the bottom of the container with the suction pump before any part of his body disturbs the sediment;
   (G) the equipped person attaining footing on the cleaned spot; and
   (H) the said equipped person removing the remainder of sediment on the bottom of the container with the suction pump.

9. The method of claim 8, wherein the cleaning person and the apparatus is sanitized by soaking and washing in a sodium hypochlorite solution.

10. The method of claim 8, wherein the cleaning person and the apparatus is sanitized by soaking for 0 to 15 minutes in a 0.2 to 0.5 percent by weight sodium hypochlorite solution.

11. The method of claim 1, wherein the cleaning person is sanitized by spraying with a 0.2 to 0.5 percent by weight sodium hypochlorite solution.

12. The method of claim 3, wherein the cleaning person and the apparatus is sanitized by spraying with a 0.2 to 0.5 percent by weight sodium hypochlorite solution.

13. The method of claim 8, wherein the cleaning person is sanitized by spraying with a 0.2 to 0.5 percent by weight sodium hypochlorite solution.

14. The method of claim 8, wherein the cleaning person and the apparatus is sanitized by spraying with a 0.2 to 0.5 percent by weight sodium hypochlorite solution.

* * * * *